United States Patent
Powell et al.

(10) Patent No.: US 9,382,633 B2
(45) Date of Patent: *Jul. 5, 2016

(54) SYSTEMS AND METHODS OF IMPROVED FERMENTATION

(71) Applicant: Colorado Energy Research Technologies, LLC, Englewood, CO (US)

(72) Inventors: Wayne J. Powell, Centennial, CO (US); Robert D. Boehmer, Centennial, CO (US); Lee L. Johnson, Littleton, CO (US)

(73) Assignee: Colorado Energy Research Technologies, LLC, Englewood, CO (US)

( * ) Notice: Subject to any disclaimer, the term of this patent is extended or adjusted under 35 U.S.C. 154(b) by 11 days.

This patent is subject to a terminal disclaimer.

(21) Appl. No.: 14/136,292

(22) Filed: Dec. 20, 2013

(65) Prior Publication Data

US 2014/0174944 A1 Jun. 26, 2014

Related U.S. Application Data

(63) Continuation-in-part of application No. 13/727,226, filed on Dec. 26, 2012, now Pat. No. 8,765,452.

(60) Provisional application No. 61/745,363, filed on Dec. 21, 2012, provisional application No. 61/807,674, filed on Apr. 2, 2013.

(51) Int. Cl.
*C25B 3/00* (2006.01)
*C25B 3/02* (2006.01)

(52) U.S. Cl.
CPC .............. *C25B 3/02* (2013.01); *C12P 2201/00* (2013.01)

(58) Field of Classification Search
CPC ...... C12M 27/24; C12M 29/08; C12M 35/02; C25B 3/00; C25B 3/02; C02F 1/467; C02F 2101/30; C02F 2201/4611; C02F 2201/461752; C12P 2201/00
USPC ................... 435/173.8, 285.2; 127/1, 36, 37; 422/186.04, 186.21; 204/748.1, 671, 204/660, 663; 205/744, 755, 698, 689, 421
See application file for complete search history.

(56) References Cited

U.S. PATENT DOCUMENTS

| 4,752,364 | A | 6/1988 | Dhooge |
| 5,733,413 | A | 3/1998 | Lawson |
| 6,139,684 | A | 10/2000 | Lawson et al. |
| 6,187,842 | B1 | 2/2001 | Kobayashi et al. |
| 6,238,523 | B1 | 5/2001 | Lawson |
| 7,611,620 | B2 | 11/2009 | Carson et al. |
| 7,648,498 | B2 | 1/2010 | Hempel |
| 7,695,534 | B2 | 4/2010 | Lawson et al. |
| 7,722,755 | B2 | 5/2010 | Lawson et al. |
| 8,062,428 | B2 | 11/2011 | Blair et al. |
| 8,110,667 | B2 | 2/2012 | Zhang et al. |
| 8,173,406 | B1 | 5/2012 | Wang et al. |
| 8,252,921 | B2 | 8/2012 | Vignon et al. |
| 8,314,231 | B2 | 11/2012 | Baures et al. |
| 8,324,374 | B2 | 12/2012 | Kawasaki |
| 8,324,376 | B2 | 12/2012 | Binder et al. |
| 8,569,050 | B1 | 10/2013 | Ericsson |
| 8,765,452 | B1 * | 7/2014 | Powell et al. ............... 435/285.2 |
| 2002/0121352 | A1 | 9/2002 | Lawson et al. |
| 2008/0006536 | A1 | 1/2008 | Cuomo et al. |
| 2008/0131947 | A1 | 6/2008 | Wicking |
| 2008/0311639 | A1 | 12/2008 | Navapanich et al. |
| 2009/0264320 | A1 | 10/2009 | Hsieh et al. |
| 2010/0112424 | A1 | 5/2010 | Hayashi |
| 2010/0204068 | A1 | 8/2010 | Kesavan et al. |
| 2011/0130561 | A1 | 6/2011 | Miyashita |
| 2011/0250638 | A1 | 10/2011 | Sjoede et al. |
| 2012/0052543 | A1 | 3/2012 | Yoon |
| 2012/0100577 | A1 | 4/2012 | Medoff et al. |
| 2012/0172588 | A1 | 7/2012 | Qiao et al. |
| 2012/0232264 | A1 | 9/2012 | Sato et al. |
| 2012/0282656 | A1 | 11/2012 | Gibbs |
| 2013/0087466 | A1 * | 4/2013 | Dopp ............................. 205/698 |

FOREIGN PATENT DOCUMENTS

| DE | 102010007164 | 8/2011 |
| EP | 0041373 | 5/1981 |
| JP | 05245494 | 9/1993 |
| WO | 02/070816 | 9/2002 |
| WO | 03/092898 | 11/2003 |
| WO | WO 2006134127 A1 * | 12/2006 |
| WO | 2011/093497 | 8/2011 |
| WO | 2012000035 | 1/2012 |

OTHER PUBLICATIONS

English language machine translation of WO2006/134127 (Dec. 2006), pp. 1-45.*
Banas, T., "The Effects of Ultraviolet Radiation on Yeast", eHow.com, http://www.ehow.com/list_6375291_effects-ultraviolet-radiation-yeast.html, screen capture Dec. 26, 2012.

(Continued)

*Primary Examiner* — William H Beisner
(74) *Attorney, Agent, or Firm* — Fish & Tsang LLP

(57) ABSTRACT

Devices, systems and methods for processing cellulosic material to produce fermentable sugars are provided. Devices, systems and methods for increasing fermentation rates of microbes via biostimulation are provided. Electrodes are preferably positioned along an interior or exterior of a tube-shaped component to administer electromagnetic/electric pulses to a solution comprising a microbe. Systems can advantageously be used in new biofuels production plants, or in existing biofuels production plants without the need for significant retrofits.

19 Claims, 12 Drawing Sheets

(56) References Cited

OTHER PUBLICATIONS

Hunt, R.W. et al., "Electromagnetic Biostimulation of Living Cultures for Biotechnology, Biofuel and Bioenergy Applications", International Journal of Molecular Sciences, vol. 10, pp. 4515-4558, 2009.

Kohl, A., "What Is the Effect of UV Light on Yeast?", eHow.com, http://www.ehow.com/about_6506247_effect-uv-light-yeast_.html#ixzz259HXnucY, screen capture Dec. 26, 2012.

Preg, F. From the Test Tube to the Fuel Tank: Two Innovative Small Businesses Partner to Produce Biodiesel from Algae, AgOil International, Georgia Alternative Fuels, Sep. 1, 2009.

\* cited by examiner

SYSTEMS AND METHODS OF IMPROVED FERMENTATION

This application is a continuation-in-part of U.S. patent application Ser. No. 13/727,226, filed on Dec. 26, 2012, and also claims the benefit of priority of U.S. Provisional Application No. 61/807,674, filed on Apr. 2, 2013, and U.S. Provisional Applications No. 61/745,363, filed Dec. 21, 2012.

FIELD OF THE INVENTION

The field of the invention is fermentation technologies.

BACKGROUND

The following description includes information that may be useful in understanding the present invention. It is not an admission that any of the information provided herein is prior art or relevant to the presently claimed invention, or that any publication specifically or implicitly referenced is prior art.

Numerous efforts have been made to improve fermentation technologies. For example: U.S. Pat. No. 8,110,667 to Zhang, U.S. Pat. No. 8,324,374 to Kawasaki, U.S. Pat. No. 8,324,376 to Binder, U.S. Pat. No. 8,314,231 to Baures, U.S. Pat. No. 8,062,428 to Blair and U.S. Pat. No. 4,752,364 to Dhooge; and U.S. Patent Publication Nos. 2010/01112242 to Medoff, 2012/0232264 to Sato and 2011/0130561 to Miyashita have each apparently attempted to produce ethanol from sugars derived by cellulose waste. Unfortunately, little cellulosic ethanol production capacity exists today, and as taught in U.S. Pat. Nos. 6,419,788 and 4,461,648, microorganisms and enzymes cannot effectively attack cellulose without prior treatment because of the complex chemical structure of lignocellulosic material.

These and all other publications disclosed herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As another example, some have attempted to increase fermentation rates via techniques such as biostimulation (see e.g., *Electromagnetic Biostimulation of Living Cultures for Biotechnology, Biofuel and Bioenergy Applications*, by Ryan W. Hunt et al., *Int. J. Mol. Sci.* 2009, 10, 4515-4558; doi: 10.3390/ijms10104515.). Unfortunately, known efforts have apparently failed to increase fermentation rates by more than a modest amount, and have failed to teach, suggest or motivate an apparatus, system or method of bioelectromagnetic stimulation of microbes for production of biofuels or bioenergy on a commercial scale.

Thus, there is still a need for improved apparatus, systems and methods of (1) digesting cellulosic materials that obviate the need for harsh chemicals, high temperatures and high pressures, and (2) biostimulation of microorganisms to increase their fermentation rates for production of bioenergy.

SUMMARY OF THE INVENTION

The inventive subject matter provides apparatus, systems and methods in which cellulosic material can be processed to produce a carbohydrate using a multi-frequency electrical signal to generate free radicals at a first electrode, and using the free radicals to electrolyze, react with or break down compounds of the cellulosic material. The step of using the free radicals could occur at least in part at a pressure of less than 10 Bar, more preferably less than 5 Bar, and most preferably less than 2 Bar. Additionally or alternatively, the step of using the free radicals could occur at least in part at a temperature of less than 500° Celsius, more preferably less than 200° Celsius, and most preferably less than 100° Celsius (e.g., less than 85° Celsius, between 40-90° Celsius, etc.). Additionally or alternatively, the step of using the free radicals could occur at least in part at a pH between 2 and 12, more preferably between 3 and 11, and most preferably between 4 and 10. Additionally or alternatively, the step of using the free radicals could occur when the cellulosic material is present in a vat or similar reactor containing at least 50 wt %, more preferably at least 75 wt %, and most preferably at least 90 wt % water.

As used here, the term "multi-frequency electrical signal" means a noisy signal, i.e., a signal having lowest and highest frequencies that vary by at least one order of magnitude (i.e., the highest frequency is at least ten times greater than the lowest frequency), and typically many orders of magnitude (e.g., highest frequency could be at least one hundred times greater, at least one thousand times greater, etc.). It is contemplated that a multi-frequency electrical signal could be produced using an electrical arc, a plasma generator, a digital data file, or any other suitable methods or devices.

The multi-frequency electrical signal could be introduced into the cellulosic material at a voltage of between 500 V/cm and 15,000 V/cm, and more preferably at a voltage of between 4,000 V/cm and 8,000 V/cm. As used herein, "V/cm" means the volts used per centimeter gap between electrode pairs. For example, if an electrical signal is introduced at a voltage of 15,000 V/cm, and the gap between an electrode pair is 2 cm, then 30,000 V is used. Additionally or alternatively, the multi-frequency electrical signal could be introduced into the cellulosic material with a duty cycle of 50 to 99%, and more preferably of 75 to 95%. Additionally or alternatively, the multi-frequency electrical signal could be introduced into the cellulosic material using a flow tube (e.g., a flow tube reactor of the inventive subject matter, etc.) or similarly partially enclosed device.

It is contemplated that a catalyst (for example, a metal that supports catalysis) could optionally be added to the cellulosic material being processed. In some aspects, the first electrode could be used as an anode, and could include a metal (e.g., as a coating, etc.) selected from a group known for catalyzing chemical reactions for example the platinum group metals (i.e., ruthenium, rhodium, palladium, osmium, iridium, and platinum). Additionally or alternatively, the first electrode could cooperate with a cathode comprising a metal selected from a group consisting of a different catalytic metal, for example one or more of the transition metals.

The inventive subject matter also provides apparatus, systems and methods in which pulse driving circuitry provides electrical pulses to an interior/lumen of a reactor tube, wherein the reactor tube can be suspended (e.g., via bracket(s), etc.) or submerged in a fermentation vat to increase a rate of fermentation of a microbe. Preferably, the pulses are provided at a pulse length and duty cycle effective to increase a fermentation rate of a microorganism to an interior of the lumen.

One skilled in the art should appreciate that flow tubes were not previously used with respect to fermentation tanks because previous efforts were typically directed to generating free radicals. As such, a pump is generally used to direct fluid to a flow tube located outside of a fermentation tank. However, where efforts are to be directed to the preservation of cells, or to stimulate growth via a flow tube reactor disposed at least partially within a fermentation tank, the addition of a fluid pump (e.g., gravity pump, velocity pump, impulse pump, displacement pump, etc.) may have the effect of destroying the microbial cells.

As used herein, a duty cycle refers to a percent of time that an apparatus or system spends in an active state as a fraction of the total time under consideration (i.e., for a given time period). The total time under consideration could be an entire fermentation process, or a portion thereof (e.g., a portion wherein a first and second set of pulses are emitted having different frequencies, etc., a one hour time block, a two hour block, a 12 hour block, etc.).

It should be appreciated that using systems and methods of the inventive subject matter, a pulse length or frequency could be adjusted before, during or after a fermentation process depending on the microbes present in a liquid. For example, carbon dioxide product could be measured during a fermentation process (during inactive or active period), and a pulse length or frequency could be adjusted based on the measurement.

Contemplated reactor tubes could comprise any commercially suitable length (e.g., at least 0.1 meter, at least 0.2 meter, at least 0.5 meter, at least 0.7 meter, at least 1 meter, between 0.1-0.2 meter, between 0.1-0.5 meter, between 0.1-0.7 meter, between 0.1-1 meter, etc.), and any commercially suitable diameter (e.g., at least 1 centimeter, at least 2 centimeter, at least 5 centimeter, at least 10 centimeter, at least 15 centimeter, at least 20 centimeter, between 1-2 centimeters, between 1-5 centimeters, between 5-10 centimeters, between 10-15 centimeters, between 10-20 centimeters, between 15-25 centimeters, etc.).

The electrical pulses provided by the pulse driving circuitry could be produced at one or more electrodes. It is contemplated that some or all of the electrodes could, in some embodiments, cause fluid to move in a particular direction or a particular speed, similarly to a pump (e.g., acting as an electrostatic fluid accelerator, etc.).

The electrodes are advantageously placed along a length of the reactor tube in any suitable configuration. For example, some or all of the electrodes could be disposed with uneven spacing along the length of the reactor tube, the spacing referring to at least one of a distance between electrodes at a first length of the lumen, or a distance between electrodes along a length (e.g., at first and second different lengths, etc.). Such an uneven spacing could comprise, for example, a phi spacing, a progressively greater inter-electrode spacing along the length of the reactor tube, or any other suitable uneven spacing.

Additionally or alternatively, the electrodes could comprise different lengths from one another. For example, an electrode pair at a first portion of the reactor tube could comprise a first length, while a second electrode pair at a second portion of the reactor tube could comprise a second length, different from the first length. Additionally or alternatively, a third electrode pair at a third portion of the reactor tube could comprise a third length, different from at least one of the first length and the second length. It is contemplated that a length of electrode pairs could progressively increase depending on a placement along a length of the reactor tube.

In embodiments where there is a noisy input, an equal spacing/length in electrodes of a flow tube reactor could lead to cancelling out of the pulsed input. However, an uneven spacing or length (e.g., a phi spacing or phi length configuration, etc.) could lead to different frequencies and oscillations, or allow different currents between electrodes placed along a length of the reactor. As used herein, "phi" refers to $$\frac{a+b}{a} = \frac{a}{b} \overset{def}{=} \varphi,$$

a ratio that has a value of approximately 1.618. Specific electrode gap distances will cancel specific frequencies. An equal spacing of electrodes can cause destructive interference of the waveform. Uneven spacing allows for the propagation of many frequencies. There is a current gradient along a length. As spacing increases, the conductivity of the media changes along that length, and the resistance of the junction increases.

In some aspects of the inventive subject matter, the pulse driving circuitry could drive the electrical pulses at a frequency of at least 1 kHz, at least 5 kHz, at least 10 kHz, at least 20 kHz, or even at least 30 kHz or higher. Preferably, the electrical pulses could be provided at a frequency previously determined to be advantageous to growth of a type of microbe that is present within a liquid of a fermentation vat.

Viewed from another perspective, the inventive subject matter provides a method of increasing a rate of fermenting a fluid to produce a product (e.g., an alcoholic beverage, ethanol, etc.). The method could comprise placing components of a fluid including, among other things, one or more of carbohydrates or at least partially cellulosic waste (for example, biomass, food waste, etc.) or a slurry that includes water and carbohydrates or cellulosic waste, with at least one microbe (e.g., yeast, fungi, bacteria, archaebacteria, algae, protozoa, etc.) or a population of microbes, in a vat or other suitable reactor. Such a reactor can include one or more of provisions for mixing (e.g., a stirrer), temperature sensing and control, or sensors for monitoring parameters relevant to the fermentative process. Examples of suitable sensors include a pH sensor, a conductivity sensor, and ORP sensor, a dissolved oxygen sensor, an alcohol sensor, an optical sensor (for example, an optical sensor suitable for characterizing optical density), and so on. In some embodiments such sensors can be placed in communication with a user or a suitable automated control system for monitoring and controlling the process. A further step could comprise operating a flow tube such that a portion of the fluid within the vat flows through the tube, and the tube provides electrical pulses to the fluid flowing within a lumen of the flow tube.

Additionally or alternatively, the method could comprise one or more of maintaining a pH of the fluid no lower than 4 for at least one hour, maintaining a temperature of the fluid for no greater than 40° Celsius for at least one hour, operating a fermentation tank at below 2 atm pressure for at least one hour, pumping the fluid through the flow tube, and adjusting a pulse driving circuitry to drive the electrical pulses at a frequency previously determined to be advantageous to growth of a type of microbe present within the fluid (e.g., between 5 Hz and 5 GHz, etc.).

The inventive subject matter also provides apparatus, systems and methods in which sets of electric pulses are fed to a solution or suspension comprising cellulosic biomass, wherein a first set of electric pulses is fed at a first frequency, a second set of electric pulses is fed at a second frequency, and the second frequency is a multiple of the first frequency.

As used herein, the term "multiple" means a number Y that is n times a number X, wherein n=an integer between 0 and 10,000±5%. For example, n could equal 1, 2, 3, 4, 5, etc., or could be between 0.95 and 1.05, 1.95 and 2.05, 2.95 and 3.05, 3.95 and 4.05, 4.95 and 5.05, and so forth.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In some aspects of the inventive subject matter, a third set of electrical pulses could be fed to the solution at a third frequency, wherein the third frequency is a multiple of at least one of the first and second frequencies. Furthermore, fourth, fifth, sixth, seventh, eighth or even further sets of electrical pulses could be fed to the solution, each of which could have a frequency that is a multiple of at least one earlier set of electrical pulses.

It should also be appreciated that the inverse is also contemplated. For example, a first frequency of a first set of electrical pulses could be a multiple of a second frequency of a second, latter set of electrical pulses, and so forth.

In other aspects of the inventive subject matter, it is contemplated that a third set of electrical pulses could have a frequency that is within 5% of a frequency of a first set multiplied by a frequency of a second set. For example, where a first set has a frequency of 10 Hz, and a second set has a frequency of 6 Hz, the frequency of the third set could be 57-63 Hz.

While not wishing to be bound by any particular theory or mode of operation, it is contemplated that an optimum frequency for a particular microbe may be different depending on what stage of the life cycle the microbe is in. Where millions or billions of microbes are present in a fermentation vat, it is very likely that an optimum frequency for the various microbes (even those of the same species) could be different. Additionally or alternatively, it is contemplated that a plurality of different microbial species could be provided in a fermentation vat, each of which could have a different optimum frequency. Using methods of the inventive subject matter, it is contemplated that while some of the microbes may be damaged, many will grow exponentially.

Previous efforts have apparently failed to appreciate that a noisy signal that provides pulses of differing frequencies could be beneficial for fermentation, as the common belief is that there is a single optimum pulse frequency associated with a particular microbe. The inventors have realized that in the absence of great efforts to synchronize cell cycles, even an apparently homogeneous population of microbes contains cells in a variety of metabolic states, and at different points in their reproductive cycles, and that under such circumstances provision of a variety of frequencies can be optimal for overall results from such a mixed population.

In other aspects of the inventive subject matter, a method for processing cellulosic biomass comprises feeding a plurality of electrical pulse sets to a solution or suspension comprising a cellulosic biomass, wherein the plurality of electrical pulse sets covers a frequency range from 2-25 MHz, more preferably from 2-20 MHz, and most preferably from 8-12 MHz, possibly under an acidic condition (i.e. pH<7). It is contemplated that the plurality of electrical pulse sets could be provided as progressively higher frequency pulses. A further step could comprise processing the cellulosic biomass into fermentable carbohydrates suitable for a production of ethanol without use of an enzyme.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
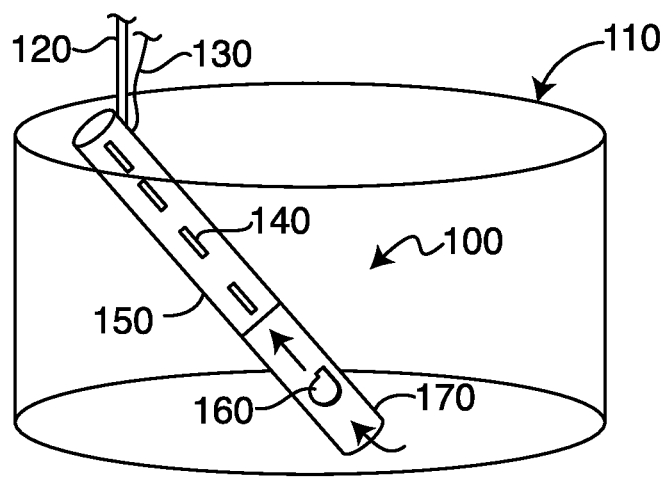
FIG. 1 is a schematic of an embodiment of a device of the inventive subject matter situated inside a fermentation tank.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter provides a flow tube reactor coupled to or including pulse driving circuitry that is configured to provide electrical pulses to an interior/lumen of the reactor tube. Some contemplated flow tube reactors could be partially or completely suspended or submerged within an existing fermentation vat to increase a rate of fermentation of a microbe.

Applicant has gathered data related to fast or accelerated fermentation processes achieved by applying high voltage pulses (e.g., 600-900 Volts) to a yeast slurry or suspension in a 1,000 mL beaker utilizing gold plated electrodes. In a particular series of experiments, 10 grams of Brewer's yeast was fed with maltose at room temperature (i.e., 25-27 degrees Celsius) as Brewer's yeast is active at room temperature. The growth rate of the yeast was calculated using the Gompertz function, which allows for the prediction of missing data relating to the transition from the lag phase to the exponential (growth) phase. The transition data is missing because the yeast cultures were inoculated in the evening and the yeast would begin to grow before measurements could start being taken. This caused the data to become logistic instead of sigmoidal, and made it difficult to accurately fit most of the commonly used microbial growth models to the data. Although growth functions such as the Monod equation are more commonly used to model microbial growth, experiments have shown that the Gompertz function is effective at modeling basic microbial growth. In the charts provided below, the units for the growth rate is given as milliliters $CO_2$ produced per minute. This is because the microbial growth rate, and thus cellular metabolism, was assumed to be directly proportional to the $CO_2$ produced through cellular respiration.

Tables 1A-C (a continuous table that is divided into three parts) below provides data relating to the experiments performed as described.

| | Voltage (volts) | Pulse Duration (millisecond) | Period (seconds) | Period (minutes) | Max Pulsed $CO_2$ Displacement (milliliters) | Max Control $CO_2$ Displacement (milliliters) | Pulsed Growth Rate (mL/min) | Control Growth Rate (mL/min) |
|---|---|---|---|---|---|---|---|---|
| 10/10 | 800 | 72 | 720 | 12 | 145 | 100 | 0.0076989 | 0.0044631 |
| 9/19 | 600 | 68 | 240 | 4 | 155 | 130 | −0.0125636 | −0.0074658 |
| 10/4 | 900 | 68 | 480 | 8 | 125 | 95 | 0.0099042 | 0.0065069 |
| 9/27 | 587 | 124 | 240 | 4 | 130 | 150 | 0.0116822 | 0.0077647 |
| 9/27 | 587 | 68 | 480 | 8 | 155 | 150 | 0.0103517 | 0.0077647 |
| 10/2 | 900 | 50 | 480 | 8 | 85 | 105 | 0.0134134 | 0.0109984 |
| 10/4 | 900 | 80 | 480 | 8 | 125 | 95 | 0.0074963 | 0.0065069 |
| 9/19 | 600 | 25 | 540 | 9 | 155 | 130 | −0.0082216 | −0.0074358 |
| 9/20 | 600 | 68 | 240 | 4 | 125 | 100 | 0.0113368 | 0.0104997 |
| 10/10 | 800 | 67 | 480 | 8 | 135 | 100 | 0.0046556 | 0.0044631 |
| 9/20 | 600 | 73 | 110 | 1.83 | 125 | 100 | 0.0099113 | 0.0104997 |
| 9/17 | 500 | 1 | 240 | 4 | 110 | 110 | −0.009399 | −0.0103842 |
| 10/2 | 900 | 67 | 480 | 8 | 125 | 105 | 0.0096466 | 0.0109984 |
| 9/17 | 500 | 25 | 540 | 9 | 125 | 110 | −0.0087034 | −0.0103842 |
| 9/28 | 395 | 58 | 480 | 8 | 103 | 85 | 0.0084078 | 0.0102637 |
| 9/28 | 395 | 48 | 480 | 8 | 100 | 85 | 0.0076341 | 0.0102637 |
| 9/13 | 600 | 1 | 240 | 4 | — | — | — | — |
| 9/14 | 600 | 1 | 240 | 4 | — | — | — | — |
| 9/13 | 600 | 25 | 110 | 1.83 | — | — | — | — |
| 9/14 | 600 | 25 | 540 | 9 | — | — | — | — |
| 10/9 | 800 | 68 | 480 | 8 | 20 | 2 | — | — |
| 10/9 | 800 | 124 | 240 | 4 | 6 | 2 | — | — |

| Experimental Run Time (minutes) | Displacement Per Minute - Pulsed (mL/min) | Displacement Per Minute - Control (mL/min) | Percent Difference From Control (Displacement) | Percent Difference From Control (Growth Rate) | Date |
|---|---|---|---|---|---|
| 540 | 0.268518519 | 0.185185185 | 45.00 | 72.50 | Oct. 10, 2012 |
| 450 | 0.344444444 | 0.288888889 | 19.23 | 67.8324294 | Sep. 19, 2012 |
| 570 | 0.219298246 | 0.166666667 | 31.58 | 52.21 | Oct. 4, 2012 |
| 420 | 0.30952381 | 0.357142857 | −13.33 | 50.45 | Sep. 27, 2012 |
| 420 | 0.369047619 | 0.357142857 | 3.33 | 33.32 | Sep. 27, 2012 |
| 450 | 0.188888889 | 0.233333333 | −19.05 | 21.96 | Oct. 2, 2012 |
| 570 | 0.219298246 | 0.166666667 | 31.56 | 15.21 | Oct. 4, 2012 |
| 450 | 0.344444444 | 0.288888889 | 19.23 | 9.33 | Sep. 19, 2012 |
| 420 | 0.297619048 | 0.238095238 | 25 | 7.972608741 | Sep. 20, 2012 |
| 540 | 0.25 | 0.185185185 | 35 | 4.313145571 | Oct. 10, 2012 |
| 420 | 0.297619048 | 0.238095238 | 25.00 | −5.60 | Sep. 20, 2012 |
| 270 | 0.407407407 | 0.407407407 | 0.00 | −9.487430611 | Sep. 17, 2012 |
| 450 | 0.277777778 | 0.233333333 | 19.05 | −12.29 | Oct. 2, 2012 |
| 270 | 0.462962963 | 0.407407407 | 13.64 | −16.19 | Sep. 17, 2012 |
| 480 | 0.214583333 | 0.177083333 | 21.18 | −16.08 | Sep. 28, 2012 |
| 480 | 0.208333333 | 0.177083333 | 17.65 | −25.61 | Sep. 28, 2012 |
| — | — | — | — | — | Sep. 13, 2012 |
| — | — | — | — | — | Sep. 14, 2012 |
| — | — | — | — | — | Sep. 13, 2012 |
| — | — | — | — | — | Sep. 14, 2012 |
| 540 | 0.037037037 | 0.003703704 | 900.00 | — | Oct. 9, 2012 |
| 540 | 0.011111111 | 0.003703704 | 200.00 | — | Oct. 9, 2012 |

| Notes |
| --- |
| Best observed displacement and growth rate |
| Gas chamber defect |
| Gas chamber defect |
| Gas chamber defect |
| Gas chamber defect |
| Sudden spike not consisten with growth pattern - Experimental error is likely |
| Low data values not consistent with experimentation - Experimental error is likely |

Table 2 below provides a summary of the experimental parameters shown above.

| | Minimum | Maximum |
| --- | --- | --- |
| Voltage (volts) | 395 | 900 |
| Pulse Duration (milliseconds) | 1 | 124 |
| Period (seconds) | 110 | 720 |
| Period (minutes) | 1.83 | 12 |
| Max Pulsed $CO_2$ Displacement (mL) | 6 | 155 |
| Max Control $CO_2$ Displacement (mL) | 2 | 150 |
| Pulsed Growth Rate (mL/min) | 0.0046556 | 0.0134134 |
| Control Growth Rate (mL/min) | 0.0044631 | 0.0109984 |
| Experimental Run Time (minutes) | 420 | 570 |
| Displacement Rate-Pulsed (mL/min) | 0.011111111 | 0.369047619 |
| Displacement Rate-Control (mL/min) | 0.003703704 | 0.357142857 |
| Percent Difference From Control (Displacement) | −19.04761905 | 45 |
| Percent Difference From Control (Growth Rate) | −25.62039031 | 72.50117631 |

While not wishing to be bound by any particular theory or mode of operation, it is contemplated that a micro or nano second (e.g., between a microsecond and a nanosecond, less than 1 microsecond, less than 5 microsecond, less than 10 microsecond, less than 100 microsecond, less than 1 nanosecond, less than 5 microsecond, less than 10 microsecond, less than 100 microsecond, etc.), high voltage spike in voltage (e.g., 500-1500 volts per centimeter (V/cm), 700-1200 V/cm, 800-1000 V/cm, 900-1100 V/cm, 550-650 V/cm, etc.) could increase a rate of fermentation.

FIG. 1 is a schematic of a flow tube reactor 170, pulse driving circuitry 150 and pump 160 of the inventive subject matter, situated inside a fermentation tank 110. In this embodiment, the flow tube reactor 170 is coupled with a pump 160 that is configured to move a fluid (e.g., a slurry, etc.) by mechanical action. Suitable pumps include centrifugal pumps, peristaltic pumps, piston pumps, or any pump configured to produce a suitable flow rate while minimizing damage to the suspended microbes. Alternatively, a passive pumping action can be provided by movement of gas bubbles through the flow tube reactor. The pump rate of apparatuses, systems and method of the inventive subject matter could comprise any suitable pump rate, wherein $$\text{Pump Rate} = \frac{n * \text{Volume of Tank}}{1 \, Hr.}$$

$0.05 \leq n \leq 1.00$. One should appreciate that a flow tube reactor 170 can have any suitable form factor, but is preferably configured as a tube with a lumen. As used herein, the terms "pulse probe," "RFR" and "flow tube reactor" are used interchangeably.

Viewed from another perspective, the fluid pump 160 coupled with the flow tube reactor of FIG. 1 is configured to direct a flow of a fluid (e.g., a solution comprising a microbe and a carbohydrate) from one portion of the reactor to another. Electrodes 140 are provided along an interior length of the reactor, which are configured to administer EPs driven by a pulse driving circuitry 150. The circuitry 150 can be coupled to a power supply configured to supply power to the circuitry via wires 130. Circuitry 150 can also be coupled to control(s) configured to allow an operator to adjust at least one of the voltage of a pulse, duration of a pulse, and a period between pulses.

The term "pulse driving circuitry" should be interpreted broadly, and can include any component comprising two or more contacts configured to create an adjustable spark gap between them. It is contemplated that a spark gap can be adjusted by changing the distance between the at least two contacts via one or more controls. The "pulse driving circuitry" may also be referred to herein as a "rectification cell" or "pulse circuitry".

Contemplated flow tube reactors 170 (and other components of a device of the inventive subject matter) can be suspended via a bracket (e.g., 120) or other mechanism, either partially or completely within or outside a fermentation tank (e.g., 110), algae pond or other bioreactor. Moreover, each component of the device can comprise any size and shape suitable for use with a new or existing bioreactor.

Devices and systems of the inventive subject matter can be configured to administer two or more Electric Pulses ("EPs") either continuously, or at predetermined or random intervals. As used herein, the terms "electric pulses" and "EPs" includes electromagnetic pulses. Some EPs are administered for less than 1 second (e.g., between 0.5-1 second, between 0.25-0.75 second, between 0.25-0.5 second, etc.), less than $\frac{1}{10}$ of a second (e.g., between 0.01-0.1 second, etc.) or even less than $\frac{1}{100}$ of a second (e.g., between 0.001-0.01 second, etc.). Moreover, some EPs are only administered less than 50 (e.g., between 1-50, between 10-40, between 20-35, between 25-35, etc.), less than 25 (e.g., between 1-25, between 5-20, between 10-15, between 10-12, etc.), less than 10 (e.g., between 1-10, between 2-8, between 3-5, etc.), or even less than 5 (e.g., between 1-5, etc.) times an hour.

Some possible forms of EP, suitable for fermentation of some microbes, can include a short-duration, direct current, high-voltage pulse. For example, a pulse length can be between 10 to 500 milliseconds, between 10-250 milliseconds, between 25 to 130 milliseconds, or even between 10 to 75 milliseconds, with voltage ranging from 50 to 10,000 V/cm, 100 to 5,000 V/cm, or even 300 to 4,000 V/cm DC. Very high efficacy has been found with a pulse length of approximately 70 milliseconds and voltages of approximately 900 V/cm.

As used herein, the term "approximately" means within 15 percent. For example, a voltage that is approximately 900 V/cm could be any voltage between 765 and 1,035 V/cm.

An astute reader should appreciate that an electric pulse produced by pulse driving circuitry of the inventive subject matter could comprise any suitable pulse shape, including for example, a square wave, sine wave, a saw-tooth wave or any other suitable shape. Additionally, resting periods between two pulses can range from less than one minute to over twenty minutes, and preferably between approximately eight and twelve minutes.

The EP(s) can be generated by pulse driving circuitry (e.g., 150), and utilized in a tube or tube-like RFR (e.g., 170). The circuitry can compose or be coupled to the device, a power supply, and one or more controls. An EP of correct frequency and resting period generated by circuitry of the inventive subject matter has been shown to shorten the time required to produce a sigmoidal growth curve of some microorganisms (e.g., yeast) by over 50% relative to a non-stimulated control. In other words, the microorganism's apparent growth/metabolic rates have been increased by approximately 150% or even more.

In some embodiments, a variable pump (e.g., 160) can be provided that allows adjustment of at least one of a flow rate and a flow direction (e.g., from top to bottom, from one end to another end, etc.). Variable pumps can comprise at least one of a variable displacement pump and variable speed pump. Pump sizes and capacities can be preferably selected relative to the size of the bioreactor with which it is used. EPs can be synchronized to the variable flow rate in order to maximize stimulation of an organism in the bioreactor. When appropriate, two or more devices can be used in conjunction with a single bioreactor. Thus, increased biological production can be achieved over a wide variety of bioreactor sizes using one or more devices of the inventive subject matter.

It is also contemplated that a device of the inventive subject matter can be used in greenhouse situations to greatly increase the growth rate of plants, especially in stimulating the growth of seedlings, for example with a hydroponic/aeroponics systems' conductive pathways. Yet another use of a device of the inventive subject matter is in increasing the growth/metabolism of bacteria. Contemplated uses can range from wastewater treatment to methane production or even composting. Numerous existing bacterial bioreactors could be used in conjunction with a device of the inventive subject matter.

From a methods perspective, technology of the inventive subject matter can comprise self-contained probe units that are fit for use in conjunction with an existing or new bioreactor, for example, a commercial fermentation tank.

Figure 2A:
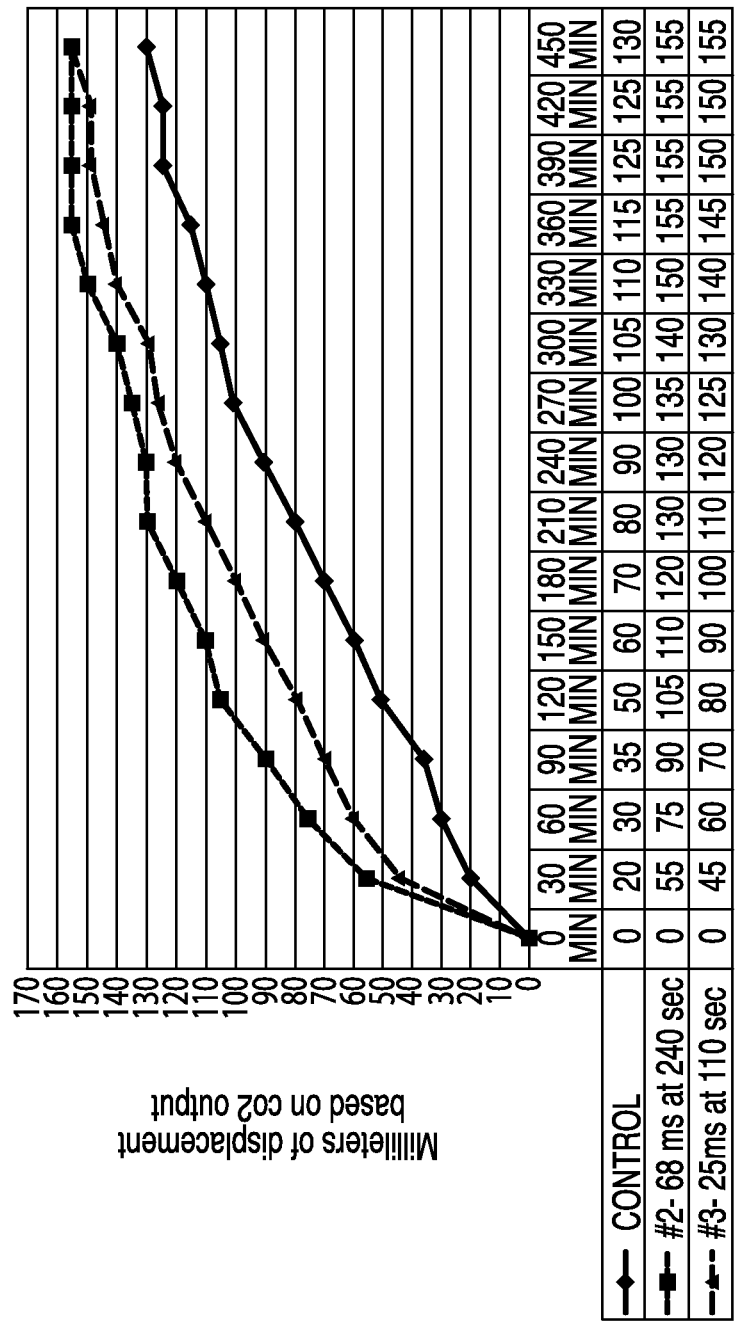
FIGS. 2A-D are graphs showing test data from tests conducted with different electrical pulses.
Figure 2B:
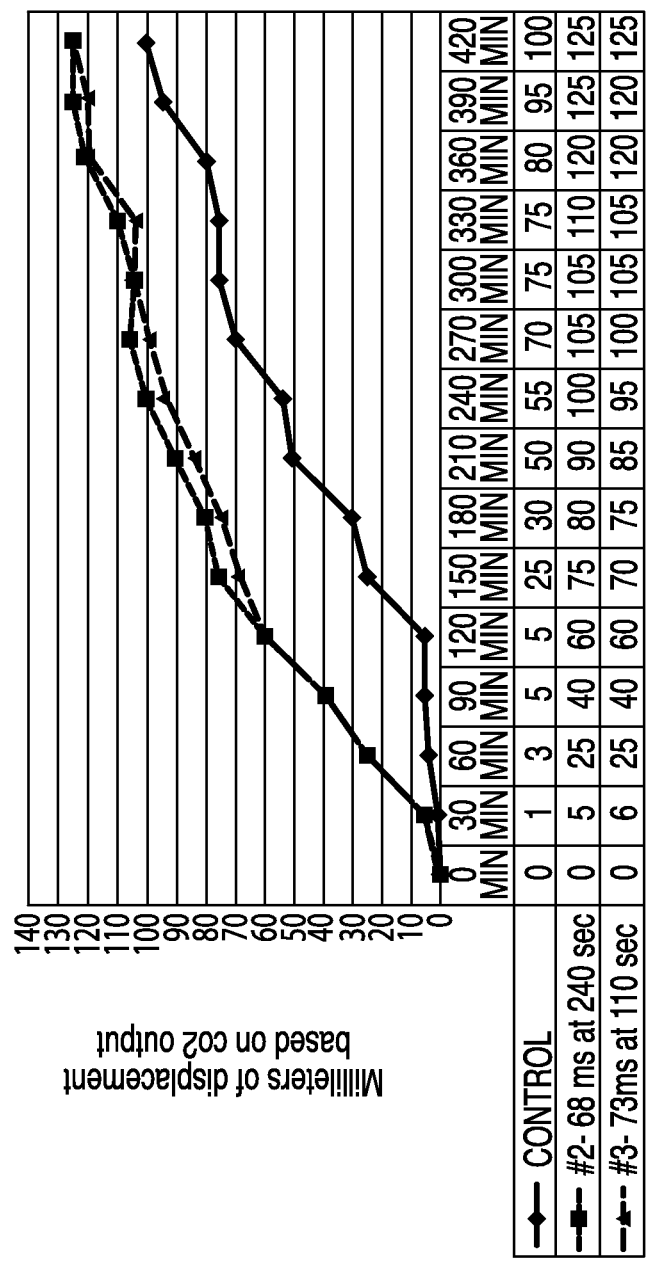
Figure 2C:
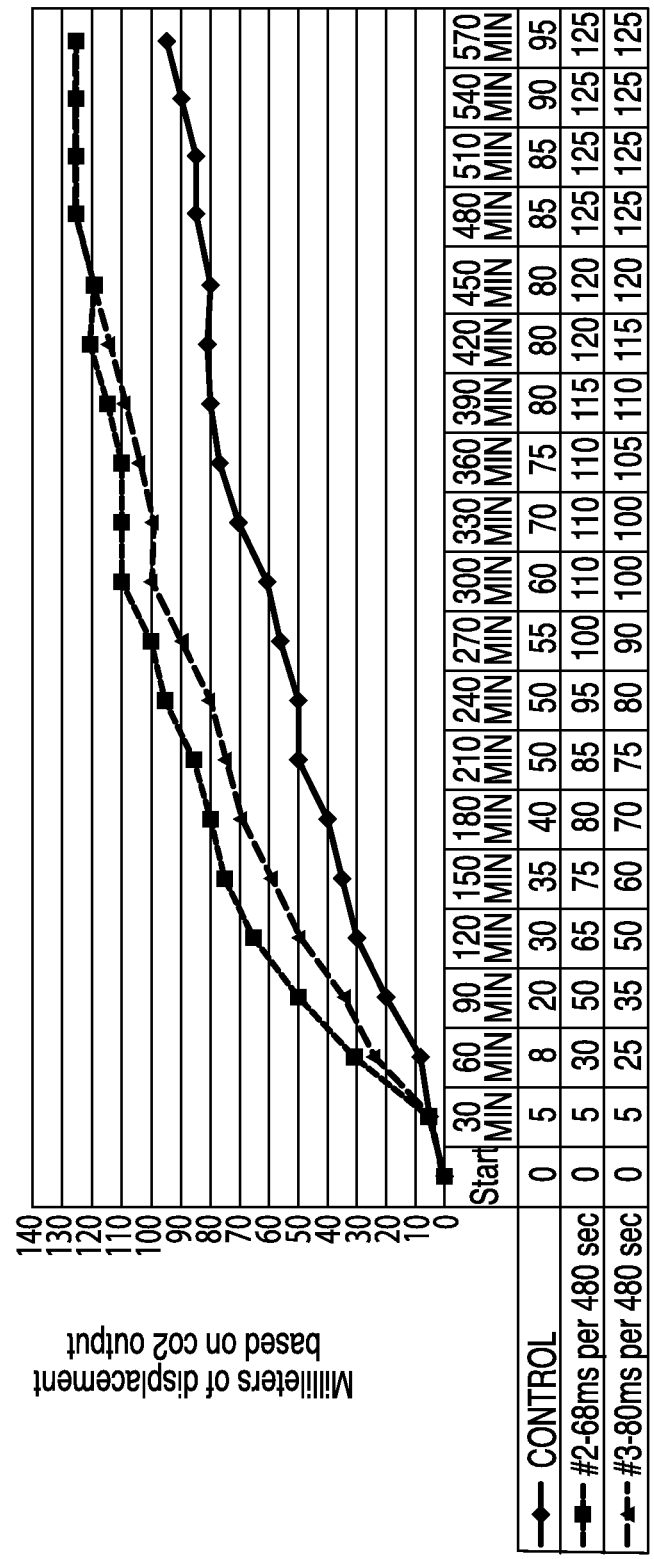
Figure 2D:
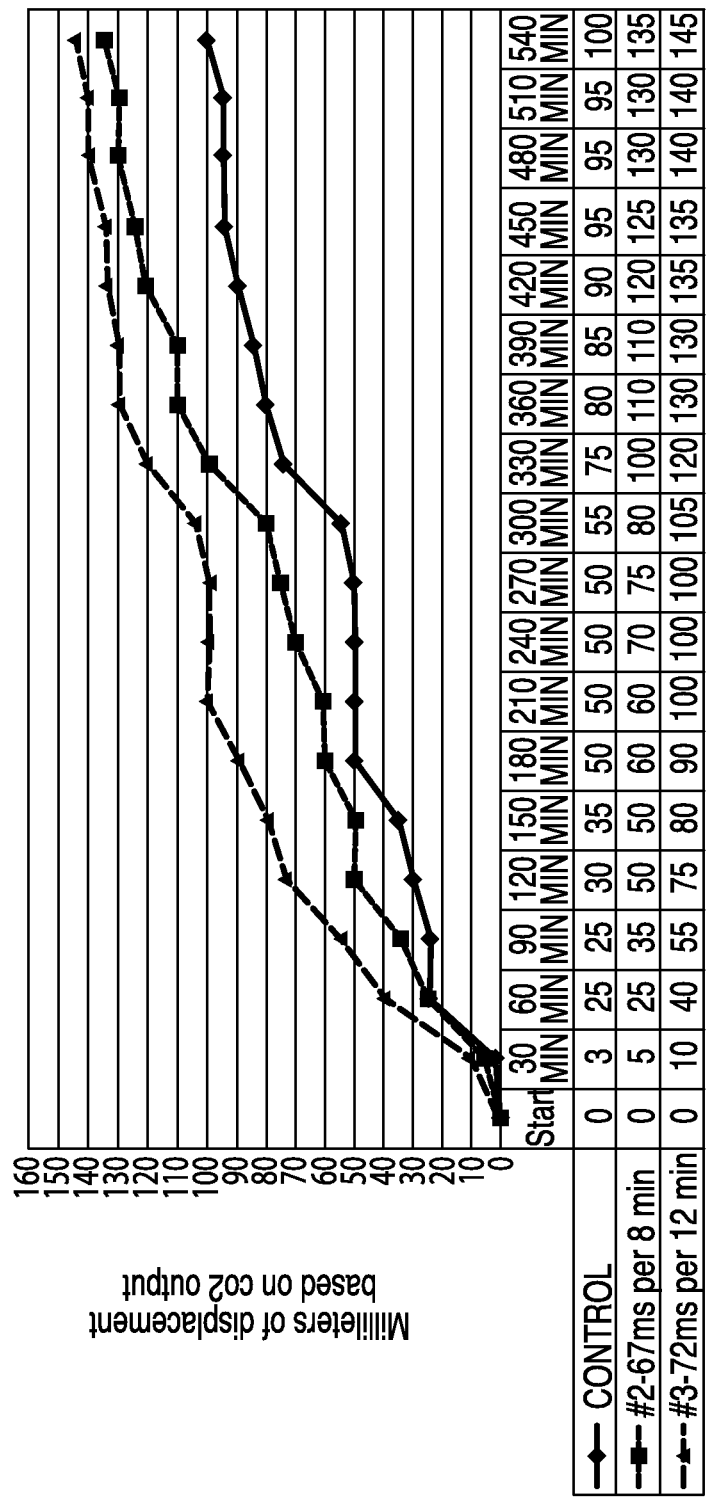

FIGS. 2A-2D show test data from various tests conducted using device(s) of the inventive subject matter with an existing bioreactor. The devices were configured to administer different EPs to a solution reacted upon by the reactor to increase the fermentation rate of microbes in the nutrient solution. The Y-axis represents milliliters of displacement based on $CO_2$ output, while the X-axis represents a time in minutes. The numerical Y-value corresponding to each 30(n) minutes is listed below the X-axis. FIG. 2A-2D correspond to EPs administered on a solution comprising the Brewer's yeast mixture described above in connection with Tables 1A-1C and Table 2. FIG. 2A corresponds to test data, conducted at 600 Volts with varying pulse lengths. FIG. 2B corresponds to test data conducted at 600 Volts with varying pulse lengths. FIG. 2C corresponds to test data, conducted at 900 Volts with varying pulse lengths. FIG. 2D corresponds to test data, conducted at 800 Volts with varying pulse lengths.

Figure 3:
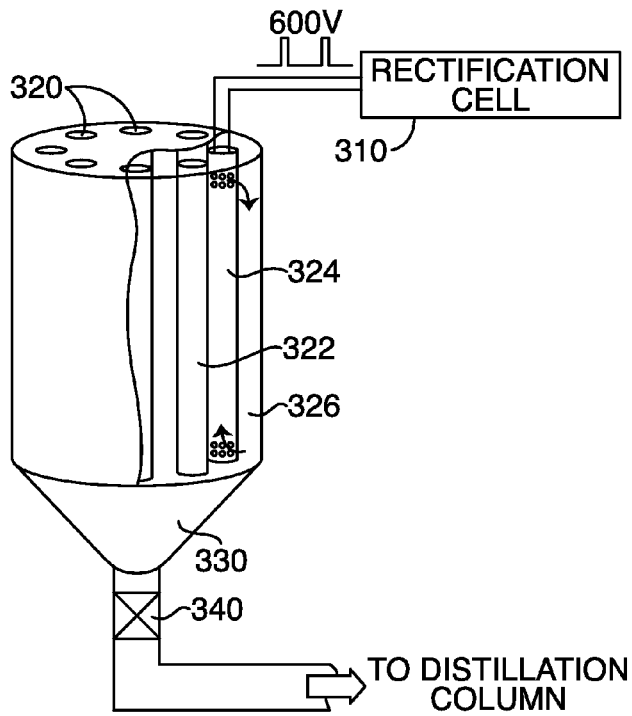
FIG. 3 is a partial cutaway schematic of a fermentation tank used in conjunction with a device or system of the inventive subject matter.

FIG. 3 shows a fermentation tank 330 used in conjunction with a system of the inventive subject matter, which comprises probes 320 (e.g., Dry EM Stimulator pulse probe 322, EM wet probe 324, etc.). Each probe (flow tube reactor, RFR, etc.) can be partially or completely submerged in a solution 326 comprising at least one of water, yeast, and sugar. A rectification cell 310 can be configured (e.g., via one or more controls) to drive high voltage electric pulses (e.g., 600V, 800V, or even 1,000 or more V, etc.) having a short duration (e.g., 1 microsecond, 5 microseconds, 10 microseconds, etc.). A control can also be configured to allow operators to control a period between pulses (e.g., 5 minutes, 10 minutes, 5 minutes between a first and second pulse and 10 minutes between a second pulse and third pulse, etc.). The device can further comprise one or more pumps configured to direct at least a portion of the solution through an RFR at a particular rate, and in a selected direction. Contemplated solutions can comprise a slurry that includes at least one of water, a microbe, and cellulosic waste (e.g., a biofuel, etc.).

It is contemplated that the flow rate of the solution, the number of probes 320, and the stimulation of EPs from the probes can be scaled to optimize, or be used in conjunction with, any suitable bioreactor and process. For example, while not limiting to the inventive subject matter, it is contemplated that where a fermentation vat includes one flow tube reactor per 1,000 to 1,000,000 L of a fluid comprising yeast, the flow rate could be between $$\text{Pump Rate} = \frac{n * \text{Volume of Tank}}{1\ Hr.}$$

$0.05 \leq n \leq 1.00$, and a pulse length could be between 1 nanosecond and 100 milliseconds.

The fermentation tank 330 can be coupled to a drain valve 340 configured to allow a solution 326 to exit fermentation tank 330 and flow to a distillation column or other apparatus, for example, upon completion of a fermentation.

In one aspect of the inventive subject matter, the solution can be maintained at a suitable pH relative to the microorganisms used. For many microorganisms (e.g., yeast, etc.), a suitable pH is contemplated to be in the range of 4 to 8, between 2 to 4, between 2 to 8, or even 6 to 8. In one aspect of the inventive subject matter, the solution can be maintained at a suitable temperature relative to the microorganisms used. For many microorganisms, a suitable temperature is contemplated to be in the range of 10 to 80° C., between 20 to 60° C., or even between 20 to 40° C. In some embodiments, parameters such as pH and temperature can be controlled using an automated system.

The fermentation tank (e.g., 330) can advantageously be operated at a pressure equal to or below 20 atm (e.g., between 1-20 atm, between 5-25 atm, etc.), equal to or below 15 atm (e.g., between 1-15 atm, between 5-10 atm, etc.), equal to or below 10 atm (e.g., between 1-10 atm, between 3-8 atm, etc.), equal to or below 5 atm (e.g., between 1-5 atm, etc.) or even equal to or below 2 atm (e.g., between 1-2 atm, etc.). Some preferred embodiments can operate at ambient (atmospheric) pressure.

Pulse driving circuitry (e.g., rectification cell 310) can be provided in a system to drive EPs at a frequency that was previously determined to be advantageous to a growth/metabolism of a type of microbe present in the solution.

Figure 4:
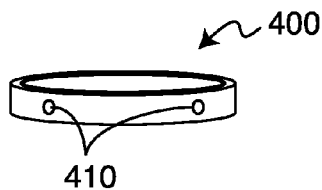
FIG. 4 is a perspective view of a probe locking collar of the inventive subject matter.

FIG. 4 shows a flow tube reactor/RFR/probe locking screw collar 400 of the inventive subject matter. The screw collar 400 provides a means for at least one of suspending and submerging the probes at least partially within a bioreactor, when desired. The collar further provides for quick and easy removal, replacement, or height adjustment of a probe. Setscrews or any other suitable collar locking mechanism (e.g., 410) of the collar can be tightened around a probe to lock it in place within a bioreactor.

Figure 5:
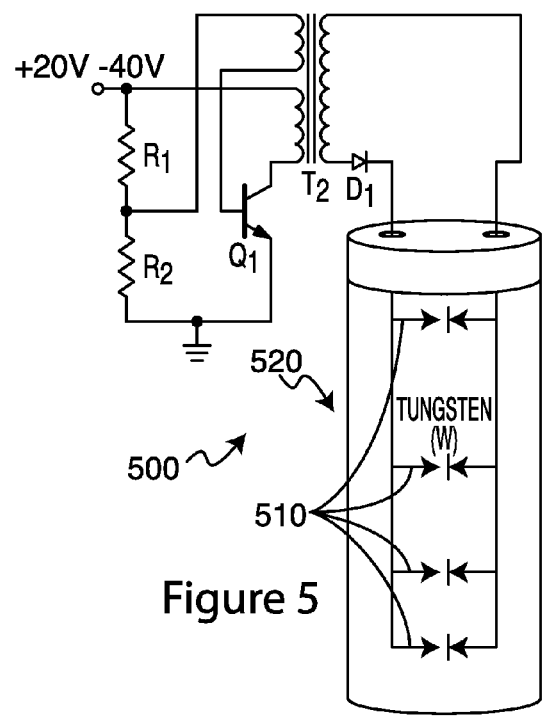
FIG. 5 is a schematic of a flow tube reactor of the inventive subject matter, with corresponding electrical circuit.

FIG. 5 shows one possible RFR (a rapid fermentation reactor) of the inventive subject matter, a dry EM Stimulator Probe 500 comprising a water-tight cylinder 520 within which a series of tungsten, aluminum, calcium, cesium carbonate, gold, lithium fluoride, molybdenum oxide, palladium, platinum, silver, nickel, iridium, a combination thereof, or other suitable metal electrodes are energized, providing a series of sparks between them, transcending up the length of the probe. These sparks produce EPs of a wide range of frequencies that can stimulate the growth/metabolism of microorganisms. Again, the power supply, the pulse driving circuitry and the controls can be integral to the probe itself. The RFR of FIG. 5 is an alternative, non-flow embodiment, with a waterproofed RF source dipped into the bulk solution. The metal electrodes described are chosen as they can readily exchange electrons, and are known or found to be catalysts.

The electrodes 510 can be disposed along a length of a probe 500 in any suitable configuration, for example, having a particular spacing (e.g., at a phi ratio). Additionally or alternatively, the electrodes 510 could have different lengths from some or all of the other electrodes within probe 500.

Figure 6:
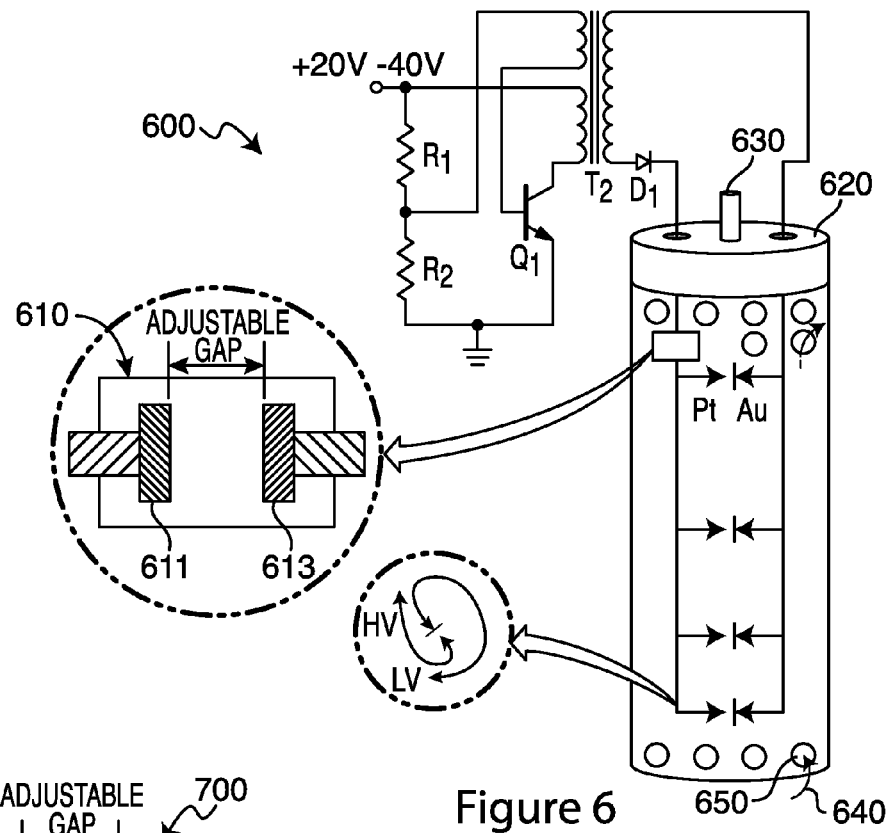
FIG. 6 is a schematic of another flow tube reactor of the inventive subject matter, with corresponding electrical circuit.

FIG. 6 shows another possible RFR of the inventive subject matter having a cylinder 620 and a vent 630. The EM Web Probe 600, like the probe of FIG. 5, can be submerged in a solution being treated 650 in a bioreactor. The probe comprises a plurality of flow holes at upper and lower ends in which the solution 650 can flow in and out of the pipe. This flow 640 can be directed or sped up via one or more pumps (e.g., an external pump). Electrodes are disposed along the inner length of the probe, and a high voltage rectification cell is disposed within the probe.

Where DC current is used, the anode preferably comprises, or is coated with, gold or platinum and the cathode preferably comprises, or is coated with, gold or platinum. These metals are selected because of their non-reactivity and high electron shell configurations. Other suitable anode materials are contemplated to include platinum metal group (PMG) and transitional conductive metals, or any alloy thereof. Other suitable cathode materials are contemplated to include PMG and transitional conductive metals, or any alloy thereof. It should be appreciated that suitable anode or cathode materials could be any conductive materials, most likely from groups 8-14, including, among other things, carbon and ceramics, and any impregnations, but other configurations are also possible. Suitably "high electron shell" atoms are those in groups 8-14. As shell height increases, ionization energy is lower. Therefore it is easier to remove electrons.

The electrode chain can be mounted on two separate semicircular assemblies, wherein rotation of these assemblies adjusts the distance between the submerged electrodes, allowing for optimization of a stimulation process. Again, the power supply, the pulse driving circuitry (e.g., rectification cell 610) and the controls can be integral to the probe itself. Rectification cell 610 comprises first and second contacts (e.g., 611, 613), which are described in further detail below.

Figure 7:
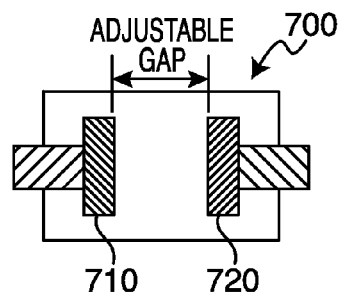
FIG. 7 is a schematic of a rectification cell of the inventive subject matter.

FIG. 7 shows a rectification cell 700 of the inventive subject matter. The rectification cell 700 can be disposed exterior to, or disposed interior to, a probe of the inventive subject matter. This rectification cell can provide a source of EPs that assists the stimulation of a fermentation process. A high voltage potential across two contacts (carbon foam impregnated with mercury, and aerogel impregnated with copper, etc.) 710 and 720 can create a spark between them. The spark(s) can provide a source of EP, and can be adjusted by changing the distance between the two contacts 710 and 720.

FIG. 8A-8D are examples of some possible flow tube reactor and pump configurations. Flow tube reactor 810 comprises a substantially straight open ended tube having a length 816 and a lumen 815. Electrodes 817 are disposed between a first wall 813 and second wall 814 of the flow tube reactor 810. Pump 811 is configured to direct a flow of a solution in a particular direction (e.g., flow direction 818).

Figure 8A:
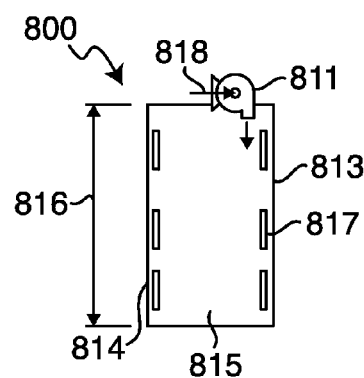
FIGS. 8A-D is a schematic of a selection of possible flow tube reactor shapes.
Figure 8B:
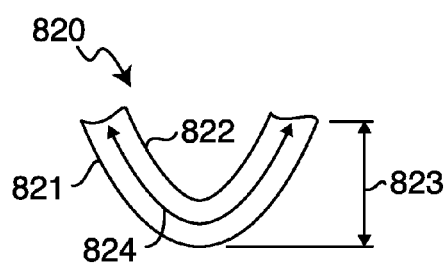

In FIG. 8B, RFR 820 comprises a curved shape having a first length 823 and a second length 824. The second length runs between first wall 821 and second wall 822 of RFR 820. A pump (not shown) pumps fluid through the device.

Figure 8C:
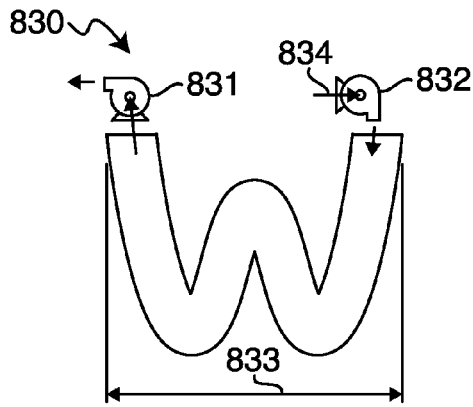

In FIG. 8C, RFR 830 comprises a multi-curved tube shape and is coupled with first pump 831 and second pump 832. In this embodiment, a solution can flow into RFR 830 in direction 834 as directed by second pump 832, then flow out of RFR 830 in direction 835 as directed by first pump 831. RFR 830 comprises a first length 833 and various other lengths (e.g., a length of a first wall, length of a second wall, length along a lumen, etc.).

Figure 8D:
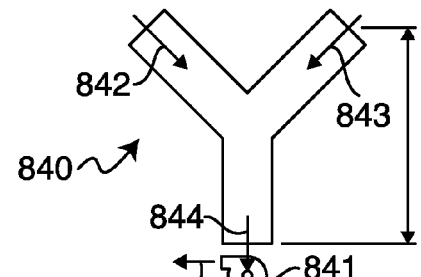

In FIG. 8D, RFR 840 comprises a substantially-Y shape and is coupled with pump 841, configured to direct a solution along flow directions 842, 843, 844 and 845. Pump 841 pumps fluid through the device. The lengths and other dimensions of each of the arms can be whatever is suitable to the application. While some possible configurations are described above, it should be appreciated that RFRs of any suitable size and shape are contemplated.

Figure 9:
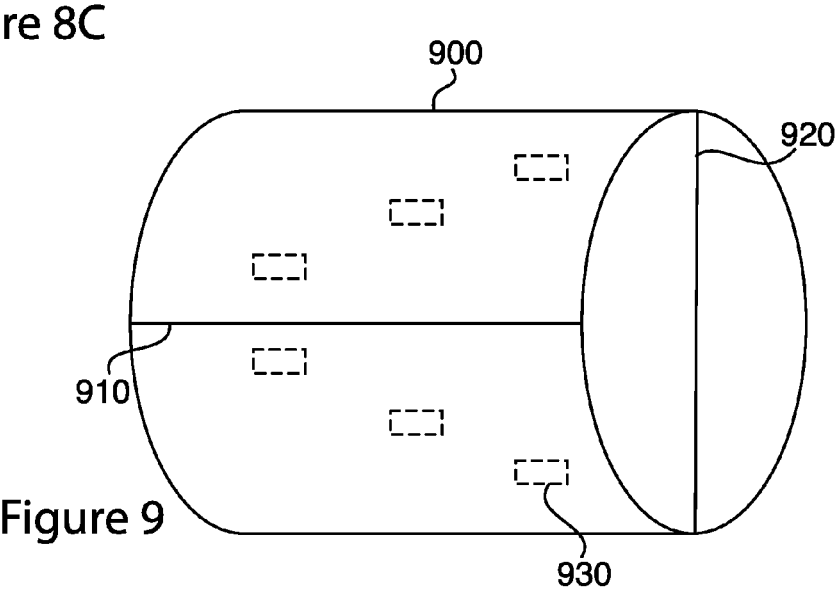
FIG. 9 is a schematic of a flow tube reactor of the inventive subject matter having a length and a diameter.

FIG. 9 illustrates a flow tube reactor 900 of the inventive subject matter. Flow tube reactor 900 comprises a length 910 and a diameter 920, and includes electrodes 930 disposed along a length therein. Electrodes 930 comprise a plurality of electrode pairs having a spacing (e.g., electrode to electrode within a pair) that progressively increases. Additionally or alternatively, it should be appreciated that a first electrode pair could be separated from at least a portion of a second electrode pair by a first portion of length 910, and that the second electrode pair could be separated from at least a portion of a third electrode pair by a second portion of length 910, wherein the first and second portions of length 910 are different.

Figure 10:
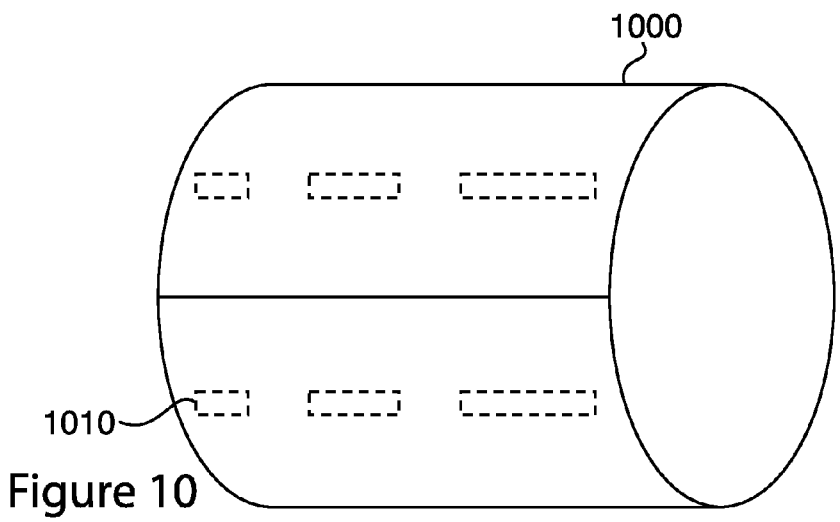
FIG. 10 is a schematic of another flow tube reactor of the inventive subject matter.

FIG. 10 illustrates another flow tube reactor 1000 of the inventive subject matter. Flow tube reactor 1000 comprises electrodes 1010 having different lengths from one another. As illustrated, a first pair of electrodes have a first length, a second pair of electrodes have a second length, and a third pair of electrodes have a third length. It is contemplated that the first length could be different from at least one of the second and third length, that the second length could be different from at least one of the first and third lengths, and that the third length could be different from at least one of the first and second lengths. For example, a first length could differ from a second length by at least 100%, at least 80%, at least 75%, at least 50%, at least 25%, and so forth. As another example, the spacing or lengths of electrodes could be determined using the phi ratio as described above.

The inventive subject matter also provides apparatuses, systems and methods for processing cellulosic biomass into fermentable sugars by providing a series of high frequency electrical pulses to the biomass, preferably in the presence of suitable microorgansims. In one aspect of the invention, a system could process cellulose biomass by providing a series of electrical pulses to a solution or suspension containing the biomass. The system is preferably configured to use the electrical pulses to reduce, oxidize, or otherwise alter the ether or carbon bonds that hold polysaccharide biomass materials together to convert the polysaccharide biomass from a polymeric form to a monomeric form. The resulting compounds are typically monosaccharide materials that can be fermented using microbes (e.g., yeast, *Saccharomyces cerevisiae, Zymomonas mobilis, Escherichia coli, Lactobacilli, Clostridium thermocellum, Clostridium ljungdahlii*, etc.) to produce ethanol.

In some embodiments, the series of electrical pulses could be provided to the solution or suspension at a frequency above 1 mega-hertz (MHz), more typically above 3 mega-hertz, and even more typically above 5 mega-hertz. More preferably, the series of electrical pulses could be provided to the solution at a frequency above 8 MHz. Even more preferably, the series of electrical pulses provided to the solution at a frequency between 8 MHz and 12 MHz.

In some embodiments, the series of electrical pulses could be provided to the solution or suspension in multiple sets. Each set of electrical pulses could be provided to the solution at a different frequency from one, some or all of the other sets. In some embodiments, it is contemplated that each set of electrical pulses could be provided to the solution or suspension at a frequency that is a multiple of a frequency of the previous set's pulses. For example, when the first set of electrical pulses is provided to the solution or suspension at 1.28 mega-hertz (MHz), the second set of electrical pulses can be provided at 2.56 MHz (twice the frequency of the first set ±5%), the third set of electrical pulses can be provided at 5.12 MHz (twice the frequency of the second set ±5%), and so forth. As another example, the frequencies can be increased from one set to another by various orders of magnitude (e.g., 1 order of magnitude (10 times), 2 orders of magnitude (100 times), 3 orders of magnitude (1,000 times), between 1-10 times, between 5-100 times, between 95-1,000 times, etc.).

The series of electrical pulses that is fed into the solution can cover a range of frequencies (e.g., from 0 MHz to 25 MHz, from 0.5 MHz to 12 MHz, from 1.28 MHz to 10.24 MHz, etc.). Preferably, the series of electrical pulses covers a frequency range from approximately 100 kilo Hertz (kHz) to 50 MHz. More preferably, the series of electrical pulses covers a frequency range from 1.28 MHz to 10.24 MHz. Even more preferably, the series of electrical pulses cover a frequency range from 8 MHz to 12 MHz, or a suitable frequency as determined by the peak output of the reaction.

In some embodiments, it is contemplated that a series of low frequency electrical pulses could be fed into the solution or suspension as one or more sets (e.g., 128±5%, 256 Hz±5%, 512 Hz±5%, 1024 Hz±5%, etc.), followed by a series of high frequency pulses. It should be appreciated that individual pulses of a set of electrical pulses does not necessarily have the same frequency. For example, it is contemplated that a set of electrical pulses could have a frequency ranging from 122-134 Hz, e.g., where each pulse of a set has a frequency within ±10% of every other pulse in the set. It should also be appreciated that the cellulosic biomass could be processed into fermentable sugars for the production of ethanol without the use of microorganisms or enzymes, which could greatly reduce the cost of cellulosic ethanol production as large amounts of expensive biological materials would not be required.

Figure 11A:
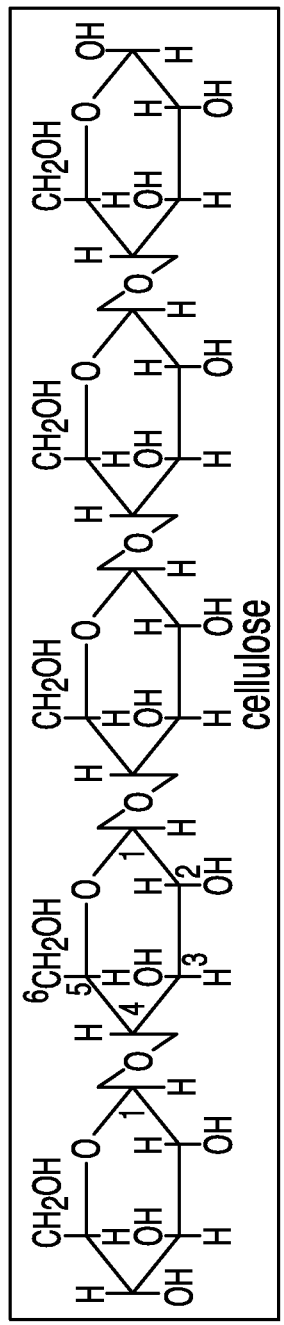
FIGS. 11A-11C are projection drawings of cellulose, amylase, and amylopectin.
Figure 11B:
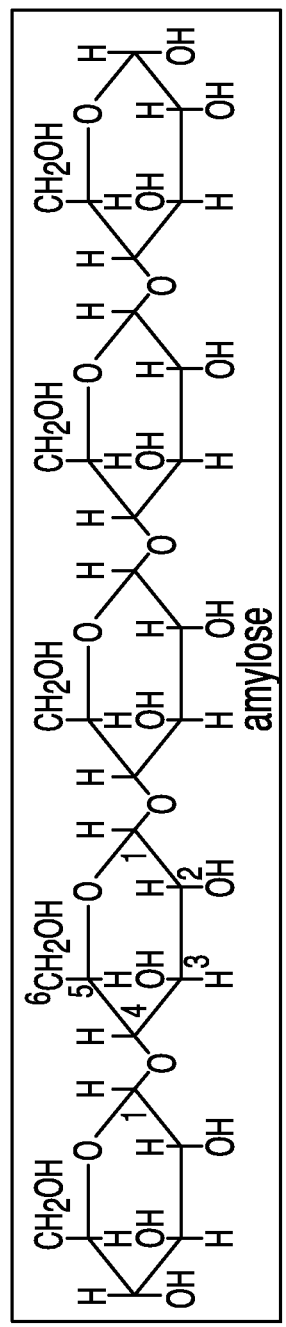
Figure 11C:
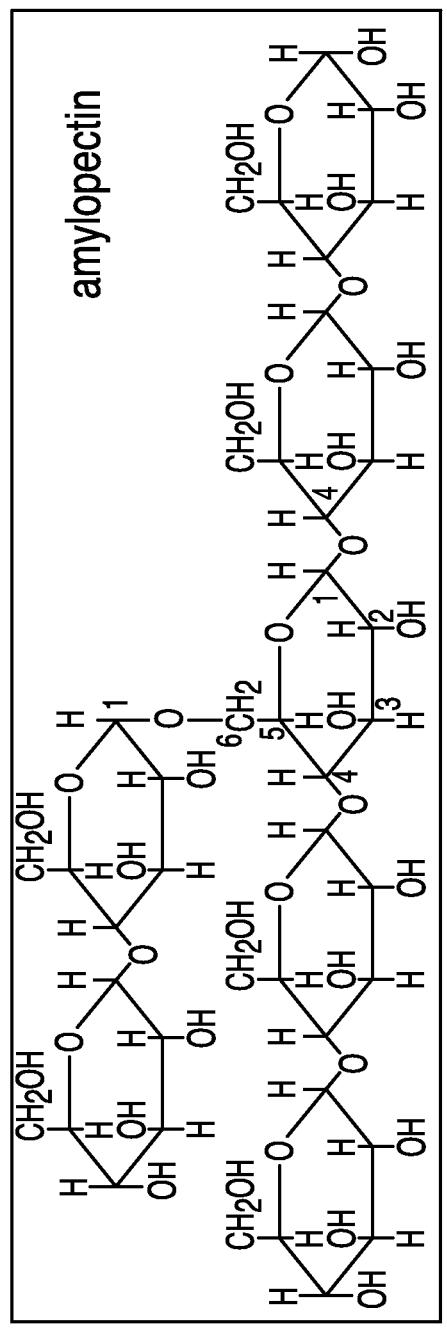

FIGS. 11A-11C illustrate the molecular structures of cellulose, amylose, and amylopectin, respectively. A cellulose polymer is composed of glucose units termed β-D-glucopyranose attached to one another at the ether by the β-1,4-glycosidic bond, as illustrated by the numbered carbons of the second glycosidic ring. In nature, bundles of parallel cellulose chains typically form, and are held together by, tight hydrogen bonding thus providing a very tough material generally found as the major component in wood, paper and cotton. Where the D-glucose residues attach to one another in a form other than a linear form via the α-1,4-glycosidic bond, the material is an α-amylose, a component of starch and shown in FIG. 11B. Another component of starch is amylopectin, a highly branched form of α-amylose shown in FIG. 11C, wherein the α-1,4-glycosidic bonds form the main chain as in α-amylose. However, a branch forms at every 24-30 glucose residues via a α-1,6-glycosidic ether bond. Glycogen is yet another material similar to amylopectin, which differs in that the branches form at every 8-12 glucose residues and the material is much larger and denser.

Hydrolysis of either the 1,4-glycosidic ether bond or the 1,6-glycosidic bond proceed by Lewis acid processes of proton donation. Historically, poly-glycosides have been hydrolyzed by high temperature acidic treatment. However, many undesirable side compounds are typically produced in addition to monoglucosides.

In some embodiments, the cellulose processing system utilizes acid catalysis by injection of a pulsed electrical source to accelerate the hydrolysis process with minimum production of side products. A solution of cellulosic material or polysaccharide could be subjected to high frequency pulses over 1 kilowatts (kw) under acidic conditions. The use of malic anhydride (or any other suitable organic or mineral acid, e.g., lactic acid, acetic acid, formic acid, citric acid, oxalid acid, uric acid, etc.) could advantageously be utilized as an acidifier so as to control side product formation with various electrode sources focusing on, for example, beryllium and platinum materials as they form small divalent ions which undergo extensive hydrolysis rendering a fairly acidic condition. Metal electrodes such as iron or aluminum form trivalent cations ($Fe^{3+}$ and $Al^{3+}$) can also be used, however their acid dissociation constant (pKa) is equivalent to that of acetic acid, which is fairly low and may not be reactive enough to be practical for some commercial uses.

The aqueous metal ion source could be a byproduct of electrolysis and contribute as a Lewis acid in the hydrolysis of cellulosic biomass to monomeric glucosides. Thus a reactive metal ion such as beryllium or platinum, a divalent metal ion, or any other suitable metal ion can be used as an optimization mechanism to the hydrolysis process.

The first hydrolysis step proceeds in general as shown in Formula 1:

$$M(H_2O)_n^{m+} + H_2O \rightleftharpoons M(H_2O)_{n-1}(OH)^{(m-1)+} + H_3O^+ \qquad (1)$$

Formula 1

The aqueous metal cation first behaves as a Bronsted-Lowry acid due to the inductive effect of the positively charged metal ion, which weakens the O—H bonds of an attached water molecule, making the liberation of a proton relatively easy. M=a metal; n=number of water molecules; and m=charge on metal ion.

Such chemical reaction in a cellulosic solution or suspension can be catalyzed in a flow tube reactor or a batch type reactor configuration of the inventive subject matter utilizing a high frequency pulse of relatively high energy injection to produce the desired mono-glucosidic residues which are needed for fermentation into ethanol production.

The inventive subject matter also provides apparatus, system and methods in which a cellulosic material is processed to produce a sugar, using a multi-frequency electrical signal to generate free radicals at a first electrode. Additionally or alternatively, a method could include a step of using the free radicals to electrolyze compounds with the cellulosic material. Such apparatus, systems and methods could include providing pulse stimulation at a frequency of between 1 kHz to 700 kHz (e.g., approximately 27 kHz, approximately 600 kHz, etc.), the frequency being at least partially dependent on the microbe providing the fermentation, and with a duty cycle of between 5 and 100% (e.g., 10-20%, etc.).

The multi-frequency electrical signal can be produced in any suitable manner, including for example, amplifying a signal from an electrical arc or other source of plasma. Such signals can have lowest and highest frequencies that vary by at least one order of magnitude, and in most cases by many orders of magnitude (e.g., 10 times, 100 times, 1,000 times, 10,000 times, 100,000 times, etc.).

The electrical signal can advantageously be introduced into the cellulosic material using voltages of between 500 V/cm and 15,000 V/cm, more preferably 800 V/cm and 10,000 V/cm, and most preferably 4,000 V/cm and 8,000 V/cm. The signal is preferably constant, but could have a duty cycle of less than 100% (e.g., 25 to 95%, 25 to 75%, 25 to 50%, 50 to 99%, 65 to 95%, 75 to 99%, 85 to 95%, 85 to 99%, etc.). It should be appreciated that the signal can be continuous, pulsed, or a combination of both.

Electrodes used in some apparatus, systems and methods of the inventive subject matter are preferably resistant to, or substantially resistant to, chemical attack or corrosion. Additionally or alternatively, the electrodes could comprise an anode that preferably includes, or is at least coated with, or an alloy of, at least one of the platinum group metals (PGM). Additionally or alternatively, one or more cathodes preferably include, or are at least coated with, or an alloy of, at least one of the transition metals.

It should also be appreciated that some apparatus, systems and methods of the inventive subject matter can operate at pressures below 10 atm, below 8 atm, below 5 atm, or even below 2 atm. Additionally or alternatively, it should be appreciated that operation is possible at temperature of less than 500° C., less than 400° C., less than 300° C., or even less than 200° C., at neutral (6.5-7.5), acidic (0-5), slightly acidic (5.01-6.49), or even basic pH (7.51-14).

An electrolyte, which can be sodium chloride, nitric acid, chloric acid, hydrochloric acid, calcium chloride, potassium nitrate, sodium hydroxide, sulfuric acid, sodium acetate, magnesium hydroxide, calcium, potassium, chlorine, magnesium, sodium, phosphate, tap water (or any other suitable gel, liquid, dry, solid ceramic or other electrolyte), may be desired or even necessary in some embodiments. Contemplated electrolytes can have any suitable pH including, for example, pH range between 4 and 10. However, preferred electrolytes are relatively neutral (pH 6 to 8) to obviate the need for neutralization prior to addition of microbes for subsequent fermentation.

Figure 12:
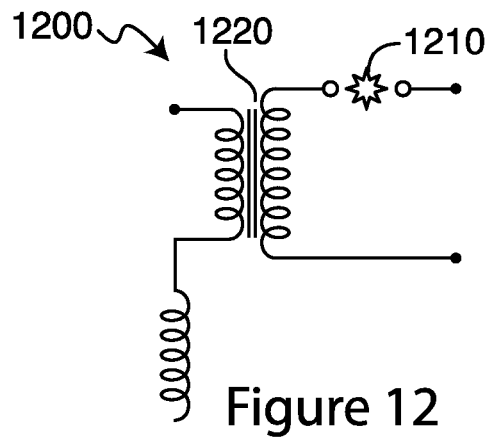
FIG. 12 illustrates a driving circuit including a spark gap that generates a signal having a wide range of frequencies (e.g., a multi-frequency electrical signal, etc.).

In FIG. 12, a driving circuit 1200 generally includes a spark gap 1210 that generates a signal having wide range of frequencies, and a transformer 1220 that increases the voltage of the signal. The spark gap 1210 could produce a very wide spectrum of frequencies, ranging from resonant frequency (likely in the kHz range) to wide radio frequency (RF). The wide range of frequencies is thought to be useful in generating many different types of free radicals in the slurries/suspensions of FIGS. 13A-13B. Spark gap 1210 could in some embodiments be replaced by an electronic signal generator that also generates a wide range of frequencies. Additionally or alternatively, it is contemplated that the frequency spread could advantageously be wide enough that the highest frequencies generated are at least 10× that of the lowest frequencies, and more preferably 2-10 or even more harmonic orders of magnitude higher than the lowest frequencies.

The transformer can advantageously provide a current for use in slurry process tanks at between 500 V/cm and 15,000 V/cm, more preferably 800 V/cm and 10,000 V/cm, and most preferably 4,000 V/cm to 8,000 V/cm. The signal is preferably constant, but could have a duty cycle of less than 100%. The signal can be continuous or pulsed.

Figure 13A:
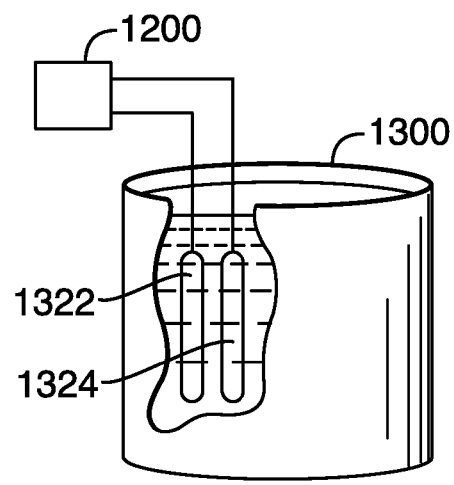
FIGS. 13A-13B illustrate a process tank having electrodes coupled to a driving circuit with and without a flow tube reactor.

In FIG. 13A, a process tank 1300 has two electrodes 1322 and 1324 coupled to the high voltage side of driving circuit 1200. The tank could contain, among other things, a slurry of ground cellulosic material suspended in water or other electrolyte.

Slurries and suspensions contemplated herein can include cellulosic materials drawn from any suitable source(s), including agricultural and lumber byproducts, wood pulp, municipal sludge, food waste, agricultural waste, animal waste, or any other suitable sources. The cellulosic materials are preferably ground or otherwise pulverized into relatively small particles (e.g., reduced to 20 to 400 screen, or more) and suspended in water or other electrolyte solution. If there is insufficient conductivity in the slurry, an electrolyte (such as those listed above) can be added to increase conductivity.

An organic acid (e.g., lactic acid, acetic acid, formic acid, citric acid, oxalid acid, uric acid, etc.) or mineral acid (e.g., HCl, $HNO_3$, $H_3PO_4$, $H_2SO_4$, $H_3BO_3$, HF, HBr, $HClO_4$, etc.) can also be added. Surprisingly, the inventors have found that decomposition of cellulosic materials can be accomplished effectively with a wide range of pH, including, for example, a pH range between 4 and 10, between 4-6, between 6-8, or between 8-10, preferably excluding a neutral pH of 7.

Experiments have also shown that decomposition of cellulosic materials can be accomplished effectively at ambient pressures. Indeed, there appears to be little or no benefit of high pressures, and some preferred pressures are below 2 atm.

Experiments have been run using various reaction temperatures, which have shown that optimum processing typically occurs at temperatures lower than 200° C. (e.g., at or about 79° C. to 90° C., etc.).

Any suitable electrodes can be used with the inventive subject matter, but electrode materials should be selected that are resistant to corrosion or chemical attack. It has been found experimentally that PGM materials work especially well as anode materials, and that transition metals work especially well as cathode materials. However, an astute reader should appreciate that an anode could comprise a transition metal, an anode could comprise PGM material(s), and that electrodes can be composed of (e.g., coated with, etc.) multiple different types of materials (e.g., alloys, etc.).

Figure 13B:
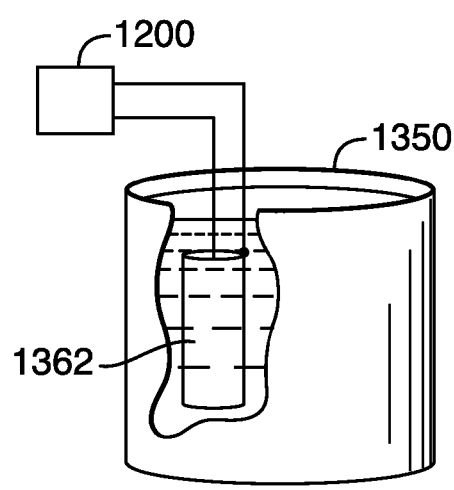

In FIG. 13B, a process tank 1350 has a flow tube reactor 1362 of the inventive subject matter submerged therein, and coupled to the high voltage side of driving circuit 1200. One or more flow tube reactors (e.g., 1, 2, 3, 4, 5, 10, 15, 20, etc. flow tube reactors) are especially contemplated for use with large vats, including those over 100,000 liters.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of processing a polysaccharide biomass to produce a monosaccharide material, comprising:
    using a multi-frequency electrical signal to generate free radicals at a first electrode;
    wherein the multi-frequency electrical signal has a highest frequency and a lowest frequency, and the highest frequency is at least a hundred times the lowest frequency; and
    using the free radicals to electrolyze compounds of the polysaccharide biomass.

2. The method of claim 1, wherein the multi-frequency electrical signal is produced using one of: an electrical arc, and a plasma generator.

3. The method of claim 1, wherein the first electrode is used as an anode and has a metal selected from a first group consisting of PMG metals.

4. The method of claim 3, wherein the first electrode cooperates with a cathode comprising a metal selected from a second group consisting of transition metals.

5. The method of claim 1, wherein the step of using the free radicals occurs at least in part at a pressure of less than 2 Bar.

6. The method of claim 1, wherein the step of using the free radicals occurs at least in part at a temperature of less than 200° C.

7. The method of claim 1, wherein the step of using the free radicals occurs at least in part at a pH between 4 and 10.

8. The method of claim 1, wherein the step of using the free radicals occurs when the polysaccharide biomass is present in a vat containing at least 90 wt % water.

9. The method of claim 1, wherein the step of using the free radicals occurs when the polysaccharide biomass is present in a vat containing at least 90 wt % water, at ambient pressure and a temperature of less than 85° C., and a pH of 4 to 10.

10. The method of claim 1, wherein the multi-frequency electrical signal is introduced into the polysaccharide biomass at voltage of between 500 V/cm and 15,000 V/cm.

11. The method of claim 1, wherein the multi-frequency electrical signal is introduced into the polysaccharide biomass at voltage of between 4,000 V/cm and 8,000 V/cm.

12. The method of claim 1, wherein the multi-frequency electrical signal is introduced into the polysaccharide biomass with a duty cycle of 75 to 95%.

13. The method of claim 1, wherein the multi-frequency electrical signal is introduced into the polysaccharide biomass using a flow tube.

14. The method of claim 1, further comprising adding a catalyst to the polysaccharide biomass being processed.

15. A method of processing a solution including cellulosic material in a fermentation vat to produce a sugar, the method comprising:
    using a multi-frequency electrical signal to generate free radicals at a plurality of electrodes placed along a length of a reactor tube that is at least one of submerged and suspended in the fermentation vat; and
    using the free radicals to electrolyze compounds of the cellulosic material.

16. The method of claim 15, wherein the first electrode is located along a length of a reactor tube.

17. The method of claim 15, wherein the step of using the free radicals occurs at least in part a pressure of less than 2 Bar.

18. The method of claim 17, wherein the step of using the free radicals occurs at least in part at a temperature of less than 200° C.

19. The method of claim 15, further comprising the step of fermenting the monosaccharide material using microbes.

* * * * *